United States Patent [19]

Bakkum

[11] Patent Number: 4,609,436

[45] Date of Patent: Sep. 2, 1986

[54] PROCESS FOR DECOLORIZING POLYETHYLENE POLYAMINES WITH A CHLORINATED HYDROCARBON

[75] Inventor: Jacobus T. M. Bakkum, Hulst, Netherlands

[73] Assignee: The Dow Chemical Company, Midland, Mich.

[21] Appl. No.: 688,776

[22] Filed: Jan. 4, 1985

[30] Foreign Application Priority Data

Jan. 6, 1984 [NL] Netherlands ............... 8400051

[51] Int. Cl.$^4$ ............... B01D 3/10; C07C 87/00
[52] U.S. Cl. .................................... 203/6; 203/67; 203/91; 202/205; 564/498
[58] Field of Search ............... 203/6, 91, 67, 68; 564/498, 482; 544/402

[56] References Cited

U.S. PATENT DOCUMENTS

| 2,543,575 | 2/1951 | Harvey et al. | 203/6 |
| 3,595,921 | 7/1971 | Pitts | 564/482 |
| 3,723,529 | 3/1973 | Pitts et al. | 564/498 |
| 3,919,054 | 11/1975 | Hands | 203/6 |
| 4,032,411 | 6/1977 | Tornquist et al. | 564/498 |
| 4,217,308 | 8/1980 | Bernady et al. | 564/498 |
| 4,264,770 | 4/1981 | Scapini et al. | 544/402 |

FOREIGN PATENT DOCUMENTS

| 0459809 | 9/1949 | Canada | 564/498 |
| 0577515 | 6/1959 | Canada | 564/482 |
| 2163516 | 12/1971 | Fed. Rep. of Germany | 564/498 |

*Primary Examiner*—S. Leon Bashore
*Assistant Examiner*—V. Manoharan
*Attorney, Agent, or Firm*—Richard G. Waterman; C. Kennth Bjork; Christopher John Rudy

[57] ABSTRACT

A process for decolorizing polyethylene polyamines using a chlorinated hydrocarbon. The discolored polyethylene polyamine and chlorinated hydrocarbon are contacted to form a decolorizing mixture, and the mixture is distilled. The decolored polyethylene polyamine is collected from the distillate.

18 Claims, No Drawings

PROCESS FOR DECOLORIZING POLYETHYLENE POLYAMINES WITH A CHLORINATED HYDROCARBON

BACKGROUND OF THE INVENTION

This invention relates to a process for decolorizing polyethylene polyamines using a chlorinated hydrocarbon.

During their production and storage, it is well-known that the polyethylene polyamines, particularly the higher polyamines, become discolored. Heretofore, various processes have been suggested to overcome the problem of discoloration of polyethylene polyamines. One such method, as described in UK No. 1,351,050 comprises reacting an aqueous solution of hydrochloric acid or an amine hydrochloride with the discolored polyethylene polyamines and distilling the resulting mixture to obtain decolored polyethylene polyamines. European Pat. No. 0,058,962 describes an alternative process in which an aqueous hydrochloric acid solution is reacted with the discolored polyethylene polyamines and the resulting mixture is flash evaporated to obtain decolored polyethylene polyamines. Unfortunately, in both processes, water is introduced into the reaction system by the addition of the aqueous acidic solution. This requires an extra processing step to remove the added water from the process thereby increasing costs and capital expenditure.

Alternative prior art processes for decolorizing the discolored polyethylene polyamines include treatment with activated carbon at elevated temperatures (about 200° C.); treatment with potassium hydroxide; and treatment with zinc metal, zinc metal and water or zinc metal and an alkali. Unfortunately, in each of these procedures, neutralization of residues, handling and separation of metal powders or reactivation of the treatment medium require special apparatus which complicate the process.

In view of the stated deficiencies in the prior art, it would be advantageous to develop an improved process for decolorizing discolored polyethylene polyamines which does not exhibit these deficiencies.

SUMMARY OF THE INVENTION

Accordingly, the present invention is a method for decolorizing a polyethylene polyamine. The method comprises contacting the discolored polyethylene polyamine with a chlorinated hydrocarbon liquid at conditions sufficient to reduce the color of the polyethylene polyamine and separating the decolored polyethylene polyamine from the mixture of the polyethylene polyamine and chlorinated hydrocarbon by distilling.

To obtain decolored polyethylene polyamine by the method of the present invention, no additional amounts of water are introduced when contacting the discolored polyethylene polyamine with the chlorinated hydrocarbon. Since no water is employed in the addition of the chlorinated hydrocarbon, no extra steps are required for its removal. Moreover, the decolorized polyethylene polyamine obtained by the practice of the present invention exhibits equivalent or better APHA color than that obtained in the prior art processes.

DETAILED DESCRIPTION OF THE INVENTION

The polyethylene polyamine to which the method of this invention is applicable includes those compounds containing one or more groups of the type —$CH_2CH_2NH$—. In general, the polyethylene polyamine compounds are linear chain compounds represented by the general formula $H_2N$—$(CH_2CH_2HN)_n$—H where n is an integer from 1 to 10, preferably 1 to 5, most preferably 2 to 5. However, the polyethylene polyamines can also be cyclic compounds such as piperazine.

Although a single polyethylene polyamine can be decolorized using the method of the present invention, in general, the method is used in decolorizing a mixture of two or more of the specified polyethylene polyamines.

The discolored polyamines to which the present invention relates can be prepared by any of the processes well-known in the art such as where a crude mixture of polyamines is produced and then subjected to refining procedures where desired individual polyamines or mixtures thereof are separated and recovered. The polyamine products recovered from the various refining or separation processes are, in general, discolored, having Gardner Color No's from about 1 to 14 or even higher.

The chlorinated hydrocarbon liquid used in decolorizing the discolored polyethylene polyamines is advantageously an alkyl chloride such as methyl, ethyl or propyl chloride or an alkylene dichloride such as methylene, ethylene or propylene dichloride. Preferably, the chlorinated hydrocarbon employed in decolorizing the polyethylene polyamines is an alkylene dichloride with ethylene dichloride most preferably being employed.

In the practice of this invention, the chlorinated hydrocarbon is employed in an amount sufficient to decolorize the polyethylene polyamines. Such amount of chlorinated hydrocarbon is dependent on a number of factors including the original color of the polyethylene polyamines, the specific chlorinated hydrocarbon employed to decolorize the polyethylene polyamines and the desired color of the decolored product. In general, the chlorinated hydrocarbon is used in an amount from 0.1 to 10.0, preferably 0.5 to 5, weight percent based on the total weight of the polyethylene polyamines being decolorized. For example, when ethylene dichloride is used to decolorize triethylene tetramine, from 2 to 5 weight percent of the ethylene dichloride based on the weight of the triethylene tetramine, has been found to be most advantageously employed.

To effectively decolorize the polyethylene polyamines, the discolored polyethylene polyamines are mixed with the chlorinated hydrocarbon and the resulting mixture is maintained at an elevated temperature of at least 60° C. for a period of time sufficient to decolorize the discolored polyethylene polyamines. The temperature and the time at which the mixture is maintained at the elevated temperature are dependent on various factors including the type and amount of chlorinated hydrocarbon and the polyethylene polyamines employed. In general, temperatures from 80° C. to 180° C., preferably from 90° C. to 180° C. and contact times from 0.25 to 3, preferably from 0.5 to 2 hours are advantageously employed.

In a specific example, when ethylene dichloride is employed to decolorize triethylene tetramine, the mixture of the ethylene dichloride and the discolored triethylene tetramine is heated to a temperature from 80° C. to 180° C., preferably from 90° C. to 180° C. for a period of from 0.5 to 2 hours, preferably from 0.75 to 1.5 hours.

The decolorized polyethylene polyamine is then separated from the polyethylene polyamine/chlorinated hydrocarbon mixture. This separation is carried out by distillation at conditions essentially the same as those employed in conventional distillation of polyethylene polyamines, i.e., a distillation temperature of below 215° C. and a pressure of less than atmospheric pressure.

The distillation temperature should not exceed 215° C. as cracking of the polyethylene polyamines will occur. An accelerated rate calorimeter test conducted on triethylene tetramine in the presence of ethylene dichloride showed a remarkable pressure increase above 215° C. because of ammonia formation. Typically, distillation is advantageously conducted at a bottom temperature of from 145° C. to 200° C. and at pressures equivalent to the vapor pressure of the polyethylene polyamine being distilled which is generally from 10 to 210 millibar (21 kPa).

The apparatus employed in the distillation of the polyethylene polyamines/chlorinated hydrocarbon mixtures can readily be selected by those experienced in the art such that the recovered polyethylene polyamines are of a desired purity.

SPECIFIC EMBODIMENTS

Having generally described the invention, the following examples are presented to illustrate and to give a more complete understanding of the invention. The examples are merely illustrative of the invention and are not intended to be limitive thereof. In the examples, all parts and percentages are by weight unless otherwise indicated.

EXAMPLE 1

To a 250-ml glass flask fitted with a 40-cm Vigieux distillation column of 2-cm diameter and containing 100 parts of triethylene tetramine having an APHA color of 50–60 were added 2.1 parts of ethylene dichloride. The resulting mixture was heated to 160° C. and maintained at this temperature for one hour. At the end of this period, the mixture was distilled. The distillation was carried out at an overhead temperature of 135° C., a bottom temperature of 145° C., a distillation pressure of 10 millibar (1 kPa) and a reflux ratio of 3. Approximately 95 percent of the discolored triethylene tetramine was recovered as an overhead product of decolored triethylene tetramine and exhibited an APHA color of 15–20.

EXAMPLE 2

Following the procedure described in Example 1 except using 4.2 parts of ethylene dichloride, triethylene tetramine having an APHA color of 50–60 was decolored. The decolored triethylene tetramine resulting from the distillation exhibited an APHA color of 10–15.

EXAMPLE 3

A discolored polyethylene polyamine having an APHA color of 50–60 was decolored following the general procedure of Example 2, except that, the distillation of the mixture of ethylene dichloride and discolored triethylene tetramine was conducted at a top temperature of 182° C., a bottom temperature of 190° C. and a distillation pressure of 80 millibar (8 kPa). The decolored triethylene tetramine obtained as an overhead product exhibited an APHA color of 10–20.

EXAMPLE 4

A discolored triethylene tetramine having an APHA color of 50–60 was decolored following the general procedure of Example 2, except that, the distillation of the mixture of ethylene dichloride and discolored triethylene tetramine, was conducted at a top temperature of 185° C., a bottom temperature of 195° C. and a distillation pressure of 82 millibar (8.2 kPa). The decolored triethylene tetramine obtained as an overhead product exhibited an APHA color of 5–7.5.

COMPARATIVE EXAMPLE A

Triethylene tetramine having an APHA color of 50–60 was distilled using a standard laboratory apparatus identical to that used in Example 1. The triethylene tetramine had not been pretreated with a chlorinated hydrocarbon and a chlorinated hydrocarbon was not present during the distillation. The distillation was conducted at an overhead temperature of 135° C., a bottom temperature of 145° C. and a distillation pressure of 10 millibar (1 kPa). The triethylene tetramine obtained as an overhead product exhibited a relatively poor APHA color of 40.

COMPARATIVE EXAMPLE B

Triethylene tetramine having an APHA color of 50–60 was decolored using the procedure described in UK No. 1,351,050. Specifically, 8.8 parts of a 35 percent aqueous solution of hydrochloric acid were added to 100 parts of the triethylene tetramine. The mixture was heated to 160° C. and maintained at this temperature for 1.5 hours. At the end of this period, the mixture was distilled using the equipment and the conditions described in Example 1. The resulting decolored triethylene tetramine exhibited an APHA color of 10–20.

The method of the present invention is shown to yield triethylene tetramine having substantially improved color. (See specifically the results of Examples 1, 2, 3 and 4 as compared with the results of Comparative Example A). Moreover, by the method of the present invention, a polyethylene polyamine can be effectively prepared having equivalent or better color than decolored polyethylene polyamine obtained by following the method of the prior art. (Comparative Example B).

I claim:
1. A process for decolorizing a discolored polyethylene polyamine which comprises contacting the discolored polyethylene polyamine with a chlorinated hydrocarbon liquid at conditions sufficient to decolorize the polyethylene polyamine and distilling the resultant mixture to separate the decolored polyethylene polyamine as an overhead product.

2. A process as claimed in claim 1 wherein the polyethylene polyamine is a linear chain compound of the general formula $H_2$—[$CH_2CH_2HN$]$_n$—H where n is an integer from 1 to 10, or a mixture of at least one polyethylene polyamines.

3. A process as claimed in claim 1 wherein the chlorinated hydrocarbon is an alkyl chloride or an alkylene dichloride.

4. A process as claimed in claim 1 wherein the chlorinated hydrocarbon is used in an amount from 0.1 to 10 percent by weight based on the total weight of the polyethylene polyamines.

5. A process as claimed in claim 1 wherein the polyethylene polyamines and the chlorinated hydrocarbon are contacted prior to distillation for a period of from 0.5 to 2 hours at a temperature of from 80° C. to 180° C. and the resulting mixture is distilled at a temperature below 215° C. to separate the decolored polyethylene polyamines.

6. A process as claimed in claim 5 wherein where the distillation bottom temperature is from 145° C. to 200° C., and the distillation pressure is from 1 to 21 kPa.

7. A process as claimed in claim 6 wherein the chlorinated hydrocarbon is an alkylene dichloride used in an amount from 0.1 to 10 percent by weight based on the total weight of the polyethylene polyamines.

8. A process as claimed in claim 7 wherein the alkylene dichloride is ethylene dichloride.

9. A process as claimed in claim 2 wherein the polyethylene polyamines and the chlorinated hydrocarbon are contacted prior to distillation for a period of from 0.5 to 2 hours at a temperature of from 80° C. to 180° C.; the resulting mixture is distilled at a temperature below 215° C. to separate the decolored polyethylene polyamines, and n is an integer from 2 to 10.

10. A process as claimed in claim 9 wherein the distillation bottom temperature is from 145° C. to 200° C., and the distillation pressure is from 1 to 21 kPa.

11. A process as claimed in claim 10 wherein the chlorinated hydrocarbon is an alkylene dichloride used in an amount from 0.1 to 10 percent by weight based on the total weight of the polyethylene polyamines.

12. A process as claimed in claim 11 wherein the alkylene dichloride is ethylene dichloride.

13. A process as claimed in claim 3 wherein the polyethylene polyamines and the chlorinated hydrocarbon are contacted prior to distillation for a period of from 0.5 to 2 hours at a temperature of from 80° C. to 180° C.; the resulting mixture is distilled at a temperature below 215° C. to separate the decolored polyethylene polyamines; and the chlorinated hydrocarbon is used in an amount from 0.1 to 5 percent by weight based on the total weight of the polyethylene polyamines.

14. A process as claimed in claim 13 where the distillation bottom temperature is from 145° C. to 200° C., and the distillation pressure is from 1 to 21 kPa.

15. A process as claimed in claim 4 wherein the polyethylene polyamines and the chlorinated hydrocarbon are contacted prior to distillation for a period of from 0.5 to 2 hours at a temperature of from 80° C. to 180° C., and the resulting mixture is distilled at a temperature below 215° C. to separate the decolored polyethylene polyamines.

16. A process as claimed in claim 15 where the distillation bottom temperature is from 145° C. to 200° C.; the distillation pressure is from 1 to 21 kPa, and the decolored polyethylene polyamine is triethylene tetramine.

17. A process as claimed in claim 16 wherein the chlorinated hydrocarbon is ethylene dichloride.

18. A process as claimed in claim 17 wherein the amount of ethylene dichloride used is from 0.5 to 5 percent based on the total weight of the triethylene tetramine.

* * * * *